United States Patent [19]

Squirrell

[11] Patent Number: 5,773,710
[45] Date of Patent: Jun. 30, 1998

[54] CELLULAR MATERIAL DETECTION APPARATUS AND METHOD

[75] Inventor: David James Squirrell, Porton Down, Great Britain

[73] Assignee: The Secretary of State for Defence in Her Britannic Majesty's Government of the United Kingdom of Great Britain and Northern Ireland, United Kingdom

[21] Appl. No.: 793,011

[22] PCT Filed: Mar. 18, 1995

[86] PCT No.: PCT/GB95/00544

§ 371 Date: Feb. 5, 1997

§ 102(e) Date: Feb. 5, 1997

[87] PCT Pub. No.: WO95/25811

PCT Pub. Date: Sep. 28, 1995

[30] Foreign Application Priority Data

Mar. 18, 1994 [GB] United Kingdom .................... 9405392

[51] Int. Cl.[6] .............................. C12Q 1/06; C12Q 1/24; G01N 33/52

[52] U.S. Cl. .......................................................... 73/28.01

[58] Field of Search ............................... 73/28.01, 28.05, 73/61.71, 31.07, 863.23; 436/164, 167, 172, 181; 422/83, 101, 144; 356/438, 441

[56] References Cited

U.S. PATENT DOCUMENTS

| | | | |
|---|---|---|---|
| 4,166,379 | 9/1979 | Bradshaw | 73/23 |
| 4,238,194 | 12/1980 | Dunham | 23/230 R |
| 4,313,848 | 2/1982 | Scott | 252/418 |
| 4,448,887 | 5/1984 | Kauffman et al. | 436/60 |
| 4,689,052 | 8/1987 | Ogren et al. | 55/17 |
| 4,794,086 | 12/1988 | Kasper et al. | 436/36 |
| 5,003,814 | 4/1991 | Crawford et al. | 73/59 |
| 5,047,221 | 9/1991 | Jozewicz et al. | 423/242 |
| 5,279,970 | 1/1994 | Patashnick et al. | 436/133 |
| 5,417,102 | 5/1995 | Prevost | 73/61.71 |
| 5,529,190 | 6/1996 | Carlton et al. | 209/170 |

FOREIGN PATENT DOCUMENTS

| | | |
|---|---|---|
| 0 101 398 | 2/1984 | European Pat. Off. . |
| 0 126 019 | 2/1984 | European Pat. Off. . |
| 60-16598 | 1/1985 | Japan . |
| 62-93634 | 4/1987 | Japan . |

*Primary Examiner*—Hezron E. Williams
*Assistant Examiner*—J. David Wiggins
*Attorney, Agent, or Firm*—Nixon & Vanderhye

[57] ABSTRACT

A method and apparatus for monitoring a gaseous environment for the presence of cellular material capable of providing a measure of presence and/or numbers of cellular microorganisms, such as bacterial cells, in a large volume of air such as in a warehouse or production facility or in an open air location where bacterial presence is suspected. The method and apparatus are particularly suited for determining the likelihood of pathogenic material being present in an environment by batch or on-line measurement of cell numbers. On-line measurement provides continuous monitoring of an environment for presence of pathogens. The device includes a continuous flow luminometer preferably fed by a cyclone or high velocity virtual impactor and lytic and luminescence reagents which detect the amount of ATP or adenylate kinase present in a sample of air.

32 Claims, 4 Drawing Sheets

CELLULAR MATERIAL DETECTION APPARATUS AND METHOD

The present invention relates to a method and apparatus for monitoring a gaseous environment for the presence of cellular material; more particularly it relates to an apparatus that is capable of providing a measure of presence and/or numbers of cellular microorganisms, such as bacterial cells, in a large volume of air such as in a warehouse or production facility or in an open air location where bacterial presence is suspected. The method and apparatus of the invention are particularly provided for determining the likelihood of pathogenic or allergenic material being present in an environment by continuous on-line measurement of cell numbers. The latter format provides a continuous monitoring of an environment.

BACKGROUND OF THE INVENTION

There is a military need for detection of the incidence of attack using biological materials, including attack using bacteria eg. in the form of cells or spores. Such need includes the capability to monitor the air some distance upwind of an asset site in order that sufficient warning may be given to personnel on that site that an attack with bacteria is imminent. In such circumstances it is required that monitoring be carried out continuously, that is for a continuous period of time for any one monitoring device eg. from several to several tens of hours.

There is a further need for determining the presence of pathogens in facilities such as hospitals and in manufacturing premises in which foodstuffs, sterile pharmaceuticals or physiological supplements are being placed in containers prior to use. Before a production run it is desirable that the sterility of the packing environment be checked for the presence of pathogens or less harmful bacteria that may be used as an indication of likely presence of pathogens or allergens.

In both of these situations it is necessary to process a large volume of air, either because of the continuous nature of the measurement or because of the need to sample a significant amount of clean room or sterile warehouse air. Furthermore in both situations it is necessary to screen for a wide range of bacteria, regardless of type, as the threat may not be that of a known genus or species.

It is known to use the luminol reaction to analyse air for the presence of haematin, but this technology is susceptible to giving readings with inorganic materials and is limited to a detection limit of $10^3$ bacterial cells in theory as only $10^{-16}$ grams of haematin is extractable from the average bacterial cell. Metal sensitivity giving high backgrounds render this system unreliable in practice.

It is known to screen for the likely presence of bacteria by analysing samples for the presence of adenosine triphosphate. This is readily carried out using luciferase and luciferin agent whereupon the presence of ATP allows luciferase to catalyse the oxidation of luciferin with the resultant emission of light. Samples are loaded into a luminometer and the amount of light emitted used as a measure of the amount of bacteria present. In order to liberate as much ATP from any cells present it is known to add a detergent to the sample in order to lyse the cells and release the ATP.

Although such biochemistry has been extensively utilised with individual samples derived by direct sampling of surfaces, liquids and solids, there has been little development of luminometry equipment suitable for monitoring bacteria in air.

JP 62093634 discloses a counter for microorganisms which draws in an air sample, collects the microorganisms from that and extracts ATP from them before assaying the ATP using a luminescent reaction. This device uses a $0.2\mu$ membrane filter to collect microorganisms from the air in a batchwise fashion, with the membrane being periodically analysed by being passed to an extracted station. No details of the sensitivity of this equipment are given, but its performance is limited by the ability of the air pump to draw sufficient sample air across the membrane and by the time taken to process the membrane microorganism content.

JP 58122281 discloses a method for detecting bacteria in air again using luminescent reagents to assay ATP. This method extracts ATP using a Tris-EDTA liquid buffer heated to 100° C. from samples of 10s of liters of air per minute batched in 10 minute samples. Filters are required to eliminate dirt and dust and these are described as essential to the method. A cooling tube is required in order to avoid increase of background noise due to raising of temperature of photomultiplier tubes use to monitor luminescence. This apparatus also uses an 'extractor' to draw air into it at 10s of liters per minute. The exact nature of this 'extractor' is not clear.

It is known to use cyclone devices to capture particulates from air, these devices typically being electrically driven and producing particulate depleted and particulate concentrated fractions. It is known to use such devices for the purposes of obtaining aerosols and other particulates from air for later analysis. For example GB 2245024 describes a cyclone for collecting a large sample volume of biological materials from the air; SU 1546481 and SU 11911460 describe use of cyclones to provide a particulate sample which is used to seed nutrient holding vessels or plates for analysis while SU 916535 collects bacteria from such cyclone on a filter band and viruses in a lower section wherefrom they are used to infect experimental animals. It is also known to use virtual impactors to collect airborne particulates, see eg. U.S. Pat. No. 4,942,297 and U.S. Pat. No. 4,670,135.

Again, none of these systems are capable of continuous monitoring of air for the presence of bacteria, particularly small amounts of pathogenic bacteria. A particular problem is the variation in concentration of fluid output from the cyclone with changes in humidity of the air being sampled. With very high throughput the cylone can run almost dry and produce high readings from a relatively normal background input.

JP 5184350 describes a system for counting of bacterial cells suspended in air which aims to shorten the determination time and improve the accuracy of the results. JP 60016598 describes an alternative device for detecting bacteria in an amount of air. JP 3112495 describes a filter system for the detection of different microorganisms floating in air. None of these devices are suitable for continuous operation.

SUMMARY OF THE INVENTION

The present inventor has now provided a truly continuous flow luminometry method and apparatus that are capable of continuous or batch monitoring of bacteria in a gaseous environment, particularly atmospheric air, such that on-line measurements may be taken of air bacteria content. Such apparatus is particularly directed at continuous monitoring but is equally suitable for sampling large volumes of air such as those inside a hospital, manufacturing facility clean room or sterile warehouse for sampling air before a production run.

BRIEF DESCRIPTION OF THE DRAWINGS

The invention is further illustrated in the attached drawings in which

DETAILED DESCRIPTION OF THE INVENTION

Figure 1:
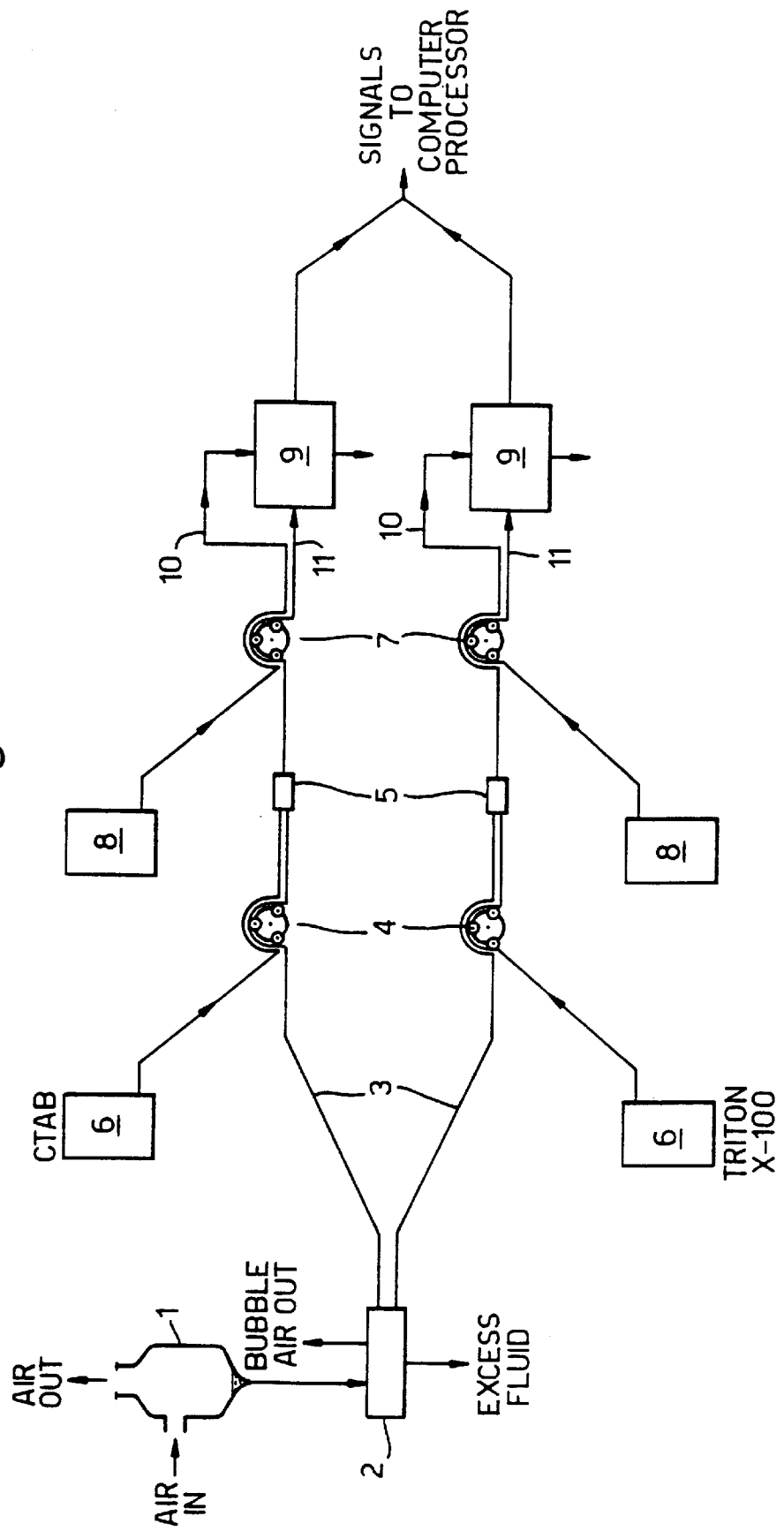
FIG. 1 is a diagrammatic representation of the invention.

In a first aspect the present invention provides a method for determining the presence and/or amount of cellular material present in a gaseous environment comprising:
(a) continuously collecting a particulate fraction from that environment over a period of time;
(b) continuously transferring the particulate fraction to a processing fluid;
(c) continuously releasing intracellular contents including ATP from cellular material present in the processing fluid containing the particulate fraction:
(d) continuously adding luminescent reagents dependent upon presence of ATP to effect luminescence to the processing fluid;
(e) continuously measuring light emitted from the processing fluid produced in (d) in a luminometer wherein a signal indicative of this light is produced by the luminometer and the presence and magnitude of the signal is equated to presence and/or amount of such material present in the gas. Preferably the signal is analysed on-line by a operator or processing device, optionally at a site remote from the place where the method is being performed.

Preferably the gas is atmospheric air, the material is bacteria, and steps (b), (c), (d) and/or (e) are carried out continuously. Preferably step (b) is carried out using a detergent, but it may be carried out by use of heat, sound or other energy source or a lytic agent, eg an enzyme, with suitable cooling effect applied if excess heat has been generated.

In order to carry out all these steps continuously it is preferred to pass the processing fluid from the collecting step to the downstream steps using a conduit, whereby the time taken for bacteria collected in step (a) to be identified as such by their ATP content is limited only by the time taken for the fluid to pass down the conduit to the luminometry steps.

More preferably the passage of fluid down the conduit is controlled by a drive means such as one or more pumps whereby a constant flow of collecting fluid may be analysed by luminometry.

For the purpose of collecting the particulate sample it is preferred to suck air into a collecting device, deposit cellular material, eg. bacteria in the form of particulates into a collecting part of the collector device and discharge particulate depleted air from the collector. Such collection is preferably carried out at a rate of some tens to thousands of liters of air per minute in order that a useful sample is taken; conveniently at 100–1000 liters per minute.

In order to differentiate between bacteria and other cellular materials such as eucaryotic cells, eg. pollens, or fungal spores it is possible to split the particulate containing processing fluid into two streams, or use two collectors to produce two processing fluid flows, and add a detergent capable of releasing cell content including ATP from all cells and spores to one fluid flow and one that is only capable of releasing the content of one of the eucaryotic cells and fungal spores to the other. For such purpose it is possible to add eg. non-ionic detergent for releasing materials from eucaryotic cells and fungal spores and eg. cationic detergent for releasing it from all cells.

By subtracting the signal from the non-ionic detergent flow luminometer from that from the cationic detergent flow luminometer it is possible to produce a continuous signal indicative of bacterial presence and numbers.

In a still more preferred method of the invention bacteria are detected by detection of the amount of adenylate kinase activity in the processing fluid containing the collected particulates, wherein adenosine diphosphate (ADP) is added to the processing fluid and is converted by any adenylate kinase present to adenosine triphosphate which in turn is detected as described above. In this manner the sensitivity of the method is increased due to the cascade effect of the enzyme's activity leading to effective amplification of signal. Such a method when applied to bacterial detection in general is the subject of the applicant's copending application PCT/GB94/00118 by the same inventor. ADP may be included in the processing fluid as it enters the particulate fraction collection step, or may be added downstream eg. with any reagents added before the luminescent reagents.

The purity of the ADP added should preferably be such that the ADP to ATP ratio in the reagent is 2000:1 or more; more preferably 6000:1 or more. The concentration of ADP in the processing fluid may in theory be any level where it is in excess of the ATP already present in the organisms if significant sensitization is to be produced. It is preferred to use at least 0.01 mM or more ADP, more preferably 0.01 to 1 mM ADP or more as the final concentration in the processing fluid.

While cellular material contains sufficient magnesium for the magnesium dependent conversion of ADP to ATP, it will be realised by those skilled in the art that the ADP reagent should preferably be used in the presence of magnesium ions if ATP is to be optimally produced. Thus the ADP reagent is preferably made up in a buffer containing sufficient magnesium to provide magnesium levels at least as two or more times the molarity as the ADP. Preferably the conversion of ADP to ATP takes place in a buffer solution of pH 5.5–8.5 buffer, more preferably pH 7.8. The provision of magnesium is particularly preferred where ADP is stabilised using EDTA or like chelating agents.

It will be realised by those skilled in the art that the term continuously as applied to step (a) herein is intended to cover the collection of particulates continuously over an operating period.

Such period may be from several minutes to many hours or may be a set period of time typically prior to operation of a sterile processing line. For use in an interior sterile space this period will be sufficient for the apparatus to have collected particulates from a volume equal to a significant proportion of the air of that space, potentially substantially all of it, and may be collected in batches.

In a preferred form of the method wherein a sterile space such as a hospital building, clean-room or sterile packing installation is being monitored the method continuously collects particulates from the air while various vents supplying air conditioned air are operated or closed down. Processing fluid corresponding to the air collected during operation of each air vent and processing fluid collected with the conditioning system off are monitored using the on-line ATP measuring capability of the method of the invention, whereby a rapid indication of the location of any contamination is provided if any of the sets of fluid show increased bacterial presence. Where collection and processing fluid production is running for the entire period of test, as opposed to just collecting batches of particulates, it is possible to merely correlate the output of the luminometer at a particular time to the presence of bacteria.

In a second aspect of the present invention there is provided an apparatus suitable for carrying out the method of the present invention.

The apparatus of the second invention comprises:
(a) a means for continuously collecting a particulate fraction from a gaseous environment;
(b) a means for continuously transferring the particulate fraction to a processing fluid;
(c) a means for continuously releasing intracellular contents including ATP from bacterial cells or spores present in the processing fluid;
(d) a means for continuously adding luminescent reagents dependent upon presence of ATP to effect luminescence to the processing fluid;
(e) a light detector means adapted to be continuously fed with the processing fluid from step (d) and capable of emitting a signal indicative of the occurence and amount of luminescence detected thereby; and
(g) a signal transmitting means for feeding the signal from the luminometer to a processor and/or display means for indicating the presence and/or amount of bacteria.

The continuous collecting means (b) is conveniently provided in the form of a cyclone or a virtual impactor, preferably a high volume virtual impactor. Where continuous monitoring of external air, ie. outside buidings, is required it is preferred to utilise a cyclone, preferably one capable of processing between 100 and 1000 liters or more of air per minute and providing a particulate fraction therefrom on a continuous basis; no upper limit is necessary however as much higher capacity cyclones will be known to those skilled in the art. Preferably the cyclone is a wet walled hydrocyclone and the particulate fraction is provided in the form of a liquid processing fluid containing particulate as it leaves the cyclone. Where a limited volume of gas is to be sampled, such as in a sterile production line unit, it may be preferred to use a high velocity virtual impactor to remove particulates from the air; such impactor might conveniently be capable of sampling about 50 to 150 liters of air per minute.

With both of these options the means for transferring the particulate fraction to processing fluid preferably comprises a supply of processing fluid into which the fraction is deposited. The processing fluid is preferably a liquid such as, water or a buffer, optionally containing magnesium ions, ADP and/or reagent for releasing intracellular contents including ATP from cells.

Where large volumes of gas are being sampled with variation in humidity it is preferred to add any detergent downstream of the collector and use a gas liquid interface that is capable of maintaining the dilution of the particulate in the processing fluid at a substantially constant level and removing excess air as bubbles. One suitable gas liquid interface is that described in copending application EP-A-668095.

A preferred modification of this interface receives liquid processing fluid under influence of a pump between the collector and interface. When the liquid level in the interface falls below a set level a level sensor transmits a signal to the pump to cause it to increase fluid flow rate. At the same time air entrained as bubbles in the liquid is allowed to escape to the atmosphere thus ensuring a reasonably constant supply of liquid to the downstream stages of the apparatus.

A further modification of this device places the pump downstream of the interface, and the pump is slowed when the interface liquid level falls below the set level such that the liquid level might recover.

The flow rate of processing fluid through the cyclone may be any flow to which a suitable amount of detergent, ADP, phosphate and luminescence reagents can be supplied without logistical problems. A convenient flow rate is from between 0.1 and 10 ml processing fluid per minute where 1000 liters of air minute is entering the collector, eg. cyclone, at the same time.

The means for releasing intracellular content including ATP may include a heater, sonic device or device for adding a lytic agent such as an enzyme or detergent as described above in the description of the method. Where the means relies on physical effect to release cell content it must produce that effect at or downstream of the means for transferring particulates to the processing liquid. Where the means adds a lytic agent it may be positioned upstream, at or downstream of the transferring means. A cooling device may be included before the downstream luminescence steps if heating is used.

The processing fluid is passed from its supply, ie. a reservoir, through the particulate transferring means and to any downstream intracellular contents releasing means by means of a fluid flow path. Preferably this is provided in the form of a liquid conduit, more preferably in the form of tubing. The processing fluid is preferably liquid moved through the conduit by means of one or more pumps and preferably these are peristaltic pumps which act upon the liquid through the conduit wall; preferred conduits being of flexible tubing type, more preferably flexible transparent plastics tubing suitable for delivering liquid under the influence of peristaltic pumps.

Using flow rates of from 0.1 to 10 ml processing fluid per minute to the cyclone, it may be expected that evaporation will reduce flow still further such that for example 0.05 to 10 ml per minute, but preferably 0.5 to 5 ml per minute, will enter the interface. At such flow rates the apparatus can conveniently use peristaltic tubing of the order of 0.25 to 3 mm internal diameter, although no particular limit is placed here other than the fact that the tubing should not be too wide to retain an air free flow through the apparatus. Suitable silicone rubber tubing for this purpose is available from Autoclude at 0.8 mm internal diameter; alternative tubing is available from Watson Marlow-UK or Ismatec-Switzerland.

Where a lytic agent is added downstream of the particulate transferring means a junction is preferably provided whereby a single peristaltic pump acts upon one or more tubes carrying processing fluid from the transferring means and one or more tubes carrying the lytic agent, preferably a solution of lytic agent; at least one of each type of tube feeding into a single downstream tube at a junction between the two.

A similar arrangement, preferably with a separate peristaltic pump, is provided for the optional addition of any ADP reagent in the adenylate kinase based aspect of the method whereby enhanced amounts of ATP are derived from a given number of bacteria and similarly for the means for adding luminescent reagents. In the latter case the junction between the conduit carrying processing fluid from step (c), with the conduit carrying luminescence reagents is preferably effected in the light measuring device itself, eg. a luminometer light measuring chamber.

Where the liquid processing fluid plus particulates is being divided into two flows for processing with different lytic agents it is possible for these to be produced by separate cyclones or impactors, at the processing fluid outlet of a single cyclone or impactor, at the air liquid interface or downstream of these. One embodiment of the apparatus of the invention provides these streams by use of a manifold downstream of the interface, and preferably uses this manifold for mixing the two lytic agents with respective ones of these streams. Thus the manifold has typically a central inlet from the interface carrying for example approximately 50% of the liquid flow input and preferably 80%. to the collector (dependent upon evaporation in the cyclone or impactor) and that is flanked by respective inlets from supplies of the two detergent reagents used at eg. 25% of that central inlet flow each. Two outlets from the manifold provide combined flows made up of 50:50 mixes of the central flow and the respective detergent flow. Typically this might be of the order of 75% to 125% of volume of the flow from the interface from each of the manifold outlets.

In a preferred embodiment of the apparatus of the invention, particularly suited to outdoor monitoring such as would be required in protecting a military asset, it is preferred to have two flows of processing fluid and treat these with different intracellular contents releasing means in order to distinguish between eucaryotic cells and fungal spores on one hand, and bacteria on the other. These flows may emanate from a single particulate collector or from two separate collectors operated at the same location. The preferred detergents used for such flows are those as described above for the method of the invention and as disclosed in PCT/GB94/00118.

In an alternative embodiment of the invention one of the luminescent agents, preferably luciferase, is immobilised near the luminometer light detector within the light measuring chamber where the processing fluid and luminescence reagents, in this case containing luciferin solution, are mixed. By being immobilised near the detector the efficiency of the detection of light may be maximised. In order to maintain the activity of the luciferase this may be fixed on a ribbon like substrate that is wound from one reel to another such that fresh luciferase is presented to the incoming fluids at a desired rate. Immobilisation may be achieved by chemically or physically linking the enzyme, eg. using a chemical linker group such as glutaraldehyde, to a suitably derivatised planar substrate, and the liquid tight nature of the chamber may be retained by introducing the ribbon of this substrate through eg. rollers that are liquid tight or are provided above the liquid level.

It will be realised that the method and apparatus of the invention may operate at ambient temperatures, but may also be operated at higher temperatures where reagent heat stability so permits. Thus the tubing or the luminometer light measuring chamber may be heated in order to increase the amount ATP produced by the ADP agent or the light emitted from the luminescent reagents in response to presence of ATP. For such use the thermostable luciferases of the applicant's copending GB applications, British Patent Application No. 940570.2, 9501170.6 and 9500660.7 (which were superseded by PCT/WO95/25780) may be used.

It will be realised by those skilled in the art that after exiting the luminometer chambers, eg. by further peristaltic tubing, the flows may be forwarded to further analytical devices such as those using specific binding to more specifically determine the nature of any bacteria present, or other agents such as viruses, DNA or chemical agents.

Further provided by the method of the invention is a tubing element or network of such elements suitable for use in the apparatus of the invention comprising a peristaltic tubing element or network of such elements characterised in that the element or network has a first tubing length with a free end suitable for attachment to the fluid outlet of an apparatus for continuously collecting a particulate fraction from a gaseous environment, preferably a gas liquid interface of such device, a junction between the other end of the first tubing length and a second tubing length, the second tubing length being suitable for connection to a source of reagent, such as a reagent container, a further tubing length provided leading from the junction of the first and second lengths having a free end suitable for connection to an inlet means of a luminometer chamber; all the lengths being capable of peristaltic action under influence of a peristaltic pump.

Preferably the element or network of the invention comprises one or more further junctions between the junction between the first and second tubing lengths with lengths of tubing having free ends suitable for connection to further sources of reagents.

Thus where detergent is used to lyse cellular material and is added upstream of the particulate collector, and bacterial ATP is being measured directly, a tubing element merely joining the interface and luminometer light measuring chamber may be used. Where the detergent is added downstream of the collector and the adenylate kinase variant of the method is being employed two junctions will be required to allow linkage with lengths of tubing from a detergent and ADP reagent source respectively. A separate luminescent reagent source and tubing may be included with the element or network as part of a reagent replenishment kit.

In each case it is preferred, by the very nature of the apparatus, that the free ends of the tubing, including those leading to reagent bottles, be covered to exclude the entry of bacteria and other cellular materials, preferably by a puncturable or removable end cover, eg. removable by tearing, cutting or pulling. Still more preferably the free ends to the reagents are actually attached to the reagents required such that a sterile replacement tubing network might be replaced all in one go with the amounts and concentrations of the various reagents being matched to each other such that they last similar lengths of operation time.

The method, apparatus and tubing element and networks of the present invention will now be exemplified by way of illustration only by reference to the following non-limiting Examples and Figures. Further embodiments of the invention falling within the scope of the claims will occur to those skilled in the art in the light of these.

FIGURES

FIG. 1 shows a diagrammatic representation of an apparatus of the invention comprising a cyclone and gas-liquid interface feeding twin lines with non-ionic and cationic detergent feeds, luminescence reagent feeds, luminometers and a central processing unit.

FIG. 2 shows a cross section through a cyclone and gas liquid interface as used in the apparatus of FIG. 1.

FIG. 3 shows a tubing element and reagent container network suitable for replacement of reagents as one unit for an apparatus as described in Example 2.

FIG. 4 is a graph of a counts per minute output of a luminometer as described in Example 1 when various amounts of ATP are added into the tubing directly downstream of the air/liquid interface.

EXAMPLES

EXAMPLE 1: Continuous Flow Luminometer Apparatus

A continuous flow luminometer apparatus of the invention was constructed using a cyclone unit (1), capable of removing particulates from approximately 1000 liters of air per minute using water as the processing fluid, connected to a gas liquid interface device (2) downstream for degassing the fluid and splitting the flow into two parallel processing flows. In this manner the liquid collects the particulates, including any aerosols, and carries them under influence of action of peristaltic pumps (4) via peristaltic tubing conduits (3) of 0.8 mm silicone rubber (Autoclude) to junctions (5) where the influence of pumps (5) draws a flow of detergent (either 0.2% aqueous CTAB solution or 0.4% aqueous Triton X-100) from containers (6) into the processing liquid flow (giving a flow concentration of 0.1% CTAB or 0.2% Triton X-100). Further pumps (7) draw the fluid flows on and deliver them at the same rate as a solution containing a flash kinetic mixture of luciferase, luciferin and buffer (Biotrace plc Bridgend, UK) from containers (8) to a light measurement chamber (not shown) within a luminometer housing (9) where the respective flows and reagents are mixed. The pumps (7) achieve synchronous delivery by acting upon delivery lines (10) and (11) simultaneously and the relative amounts of ATP released by the same particulate sample under influence of the detergents provides amounts of light and thus signals indicative of total cells/spores and eucaryotic cells/spores.

The cyclone is shown in more detail in FIG. 2, where (12) is an inlet for gas (atmospheric air) to be separated into particulate enriched and particulate depleted fractions, (13) is a supply of water processing liquid pumped at 1 ml/minute which is entrained with the air flow and passes therewith into the cyclone body main volume (14) where particulate depleted air exits under influence of an air mover (15) while processing fluid and entrapped particulates pass downward to an outlet (16) in the bottom of the cyclone. A peristaltic pump (17) passes the processing fluid to a gas liquid interface of capacity approx. 100 $\mu$l where bubbles are removed; the rate of supply of the processing fluid by the pump, or alternatively the removal of fluid by a pump downstream, being determined by the liquid level in the interface. Liquid level is determined by a liquid level sensor (not shown) and where the level falls below a set height the pump is operated to draw more processing liquid through until the desired level is restored. Excess liquid and dense particulates from the interface are removed periodically from outlet (18), air leaving the liquid as bubbles is removed via outlet (19) and processing liquid is passed under influence of a peristaltic pump (20) to the downstream tubing for addition of reagents.

As the processing liquid with particulates and detergent mixes with the luminescent reagents in the luminometer light measurement chamber, a light sensor (not shown) measures any light emitted in the chamber resultant from the presence of ATP; emission being rapid due to the flash kinetic ratio reagent having excess luciferase compared to luciferin over the ratio required for glow kinetics (where measurement is over several minutes). The luminometer transmits a signal representative of light emitted to a computer processor which in turn may display this on a display unit or compare it with control levels.

The detergents used may be standard chemicals as described above but may be provided in the form of specialist proprietary extractants such as Enzymatics ATP releasing agent, Biotrace XM extractant (Biotrace, Bridgend, UK) or Lumac NRM (Lumac BV Holland). The luminescence reagents may be standard reagents available from suppliers such as Biotrace plc and Celcis plc UK and others; the luciferase may be natural or recombinant. Concentrations of reagents are those necessary to produce flash kinetics and their ratio to the amount of cetyl trimethyl ammonium bromide treated processing liquid is that which the manufacturers recommend for batch processing taking into account the relative sizes of the tubing from each line entering the luminometer chamber. The speed of peristaltic pumps may be also adjusted to maintain ratios where separate pumps supply each flow.

EXAMPLE 2: Adenylate Kinase Measuring Continuous Flow Luminometer

A second embodiment of the luminometer of the present invention is provided wherein an additional reagent flow is included for feeding very pure adenosine diphosphate (ADP) reagent, with respect to ATP, into the processing fluid downstream of the junction (5) where detergent is added, but upstream of the luminometer. The ADP reagent (99.95% pure with respect to ATP) is added at a flow and concentration such as to produce a concentration of 0.5 mM in the final flow. The processing fluid is pH 7.4 phosphate buffered saline or TrisHCl pH 7.8 including 0.2 mM magnesium ions.

EXAMPLE 3: Tubing and Reagent Network for Apparatus of Example 2

A tubing/reagent replenishment pack provided for the apparatus of Example 2 is shown in FIG. 3. All tubing is of silicone rubber of 0.8 mm internal diameter joined at durable resilent plastics junctions dimensioned to receive them. The tubing has puncturable sealed ends for connection to one of the interface outputs at a first end (21) and to the luminometer light measuring chamber inlet at the other (22). Container (6) holds detergent reagent and has a sealable air inlet for allowing compensating air to enter as reagent is drawn out under influence of the peristaltic pump (as 4 in FIG. 1) on the tubing from the container to junction (5); this pump simultaneously acting upon tubing (3). A further piece of tubing connects junction (5) to junction (**5*a*) where a tube from a second reagent container (6*a*) carries ADP reagent under influence of a further peristaltic pump (not shown in FIG. 1). The tubing between junction (5*a*) and the end (22) is acted upon by a still further peristaltic pump (as 7 in FIG. 1**) which also acts upon a tube feeding luminescent reagent to the luminometer chamber.

In preferred apparatus the flow cells are included in the tubing pack and are also disposable; these being made of polycarbonate or polystyrene.

EXAMPLE 4: Calibration and Operation of Apparatus of Example 1 or 2

The amount of ATP present in a typical bacterial cell is of the order of $10^{-18}$ moles, equal to about $10^{-15}$ grams (see Lundin A (1989) ATP Luminescence-Rapid Methods in Microbiology ed. Stanley P E et al; Blackwell, Oxford pp 11–30; and Stanley P E (1989) J. Biolumin. Chemilum, 4, pp 375–380). Levels may be expected to be reduced in aerobic organisms when deprived of oxygen and the intracellular concentration may vary typically between 2 and 10 mM.

Calibration of the continuous flow luminometers of Example 1 and 2 may be carried out by placing known amounts of ATP into the processing fluid or cyclone while the apparatus is operating and constructing a calibration curve by plotting counts per minute of the luminometer light detector output vs amount of ATP (see FIG. 4). Alternatively known concentrations of bacteria such as Bacille Camille Guerre or *E. coli* may be aerosolised at a set distance, eg. 1 to 10 metres, away from the cyclone inlet and these amounts then plotted against luminometer output as before. Both luminometer light measurement chambers will be exposed to similar amounts of ATP where ATP is used to calibrate, whereas the non-ionic detergent chamber will receive significantly less where bacteria are used; thus a calibration using ATP and bacteria and perhaps eucaryotic cells or fungal spores may be preferable to determine all is operating as it should.

In operation the cyclone supplies particulate sample to the interface from where it is separated into two flows of equal volume and rate by the manifold, each flow containing one of the two detergents, non-ionic or cationic. The flows are mixed with the appropriate amount of ATP/phosphate reagent as required and pass to the luminometer light measurement chambers where luminescence reagents are mixed with them and light emitted. These reagents are preferably of flash kinetic type and allow almost instant emission of light which is detected by light sensors associated with the chambers which in turn pass electrical signals indicative of the amount of ATP detected to a computer processor where the two signals are used to determine the difference in signal, thus ATP, and thus bacterial cells and spores, between the two flows; this being carried out by producing an output to a display unit or printer indicative of raw luminometer output or, using software, a direct estimation of bacteria present as derived by reference to calibration curve stored in a processor associated memory.

The whole operation of the pumps may be controlled by the processor in accordance with preprogrammed regime. Thus if conditions are very dry it might be desired to alter the cyclone rate of air collection or the rate at which sample is passed to or through the interface. Alternatively supplementary collection fluid may be added at the cyclone to dilute the sample if required. Other controls involving rate of operation of one or all of the peristaltic pumps and rate of movement of tape driven immobilised luciferase may also be so controlled as will be appreciated by those skilled in the art.

Figure 2:
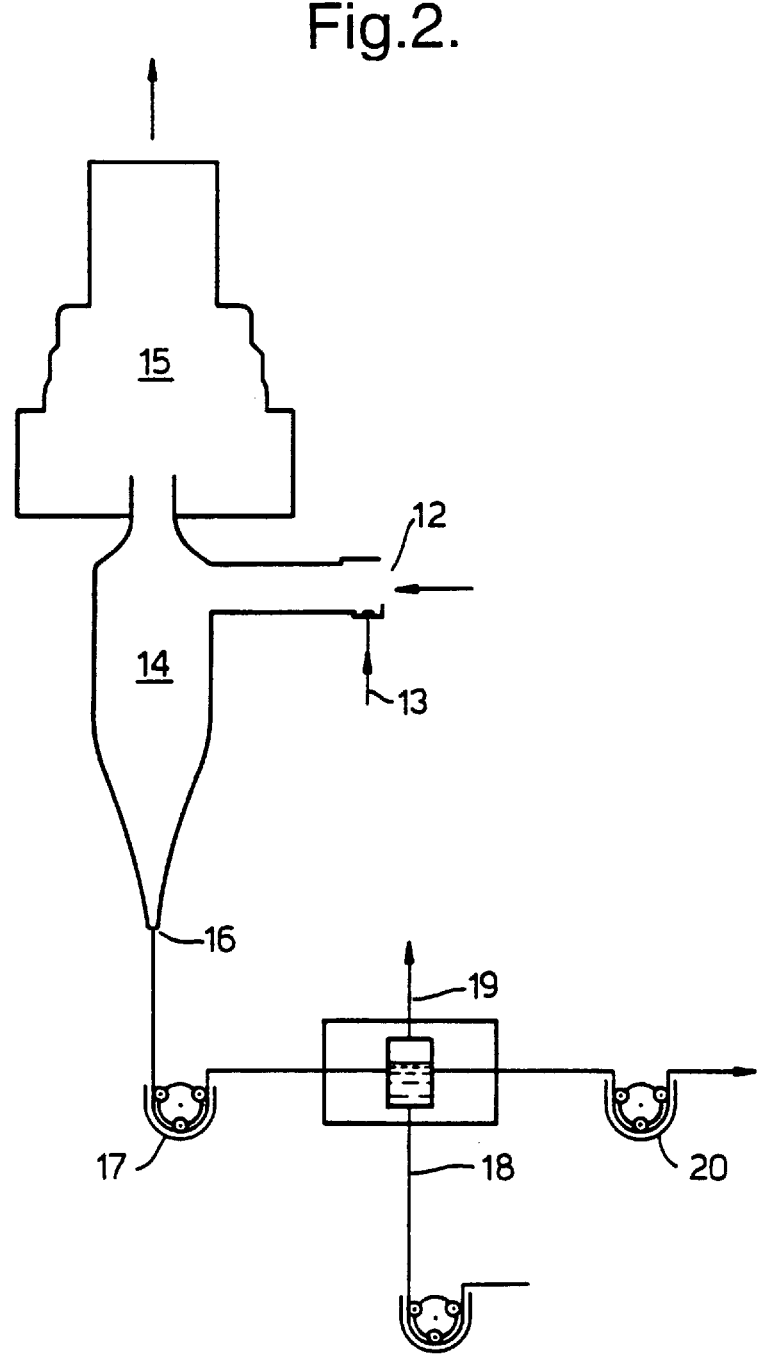
FIG. 2 is a cross-sectional view of the cyclone and gas liquid interface as used in the apparatus of FIG. 1.
Figure 3:
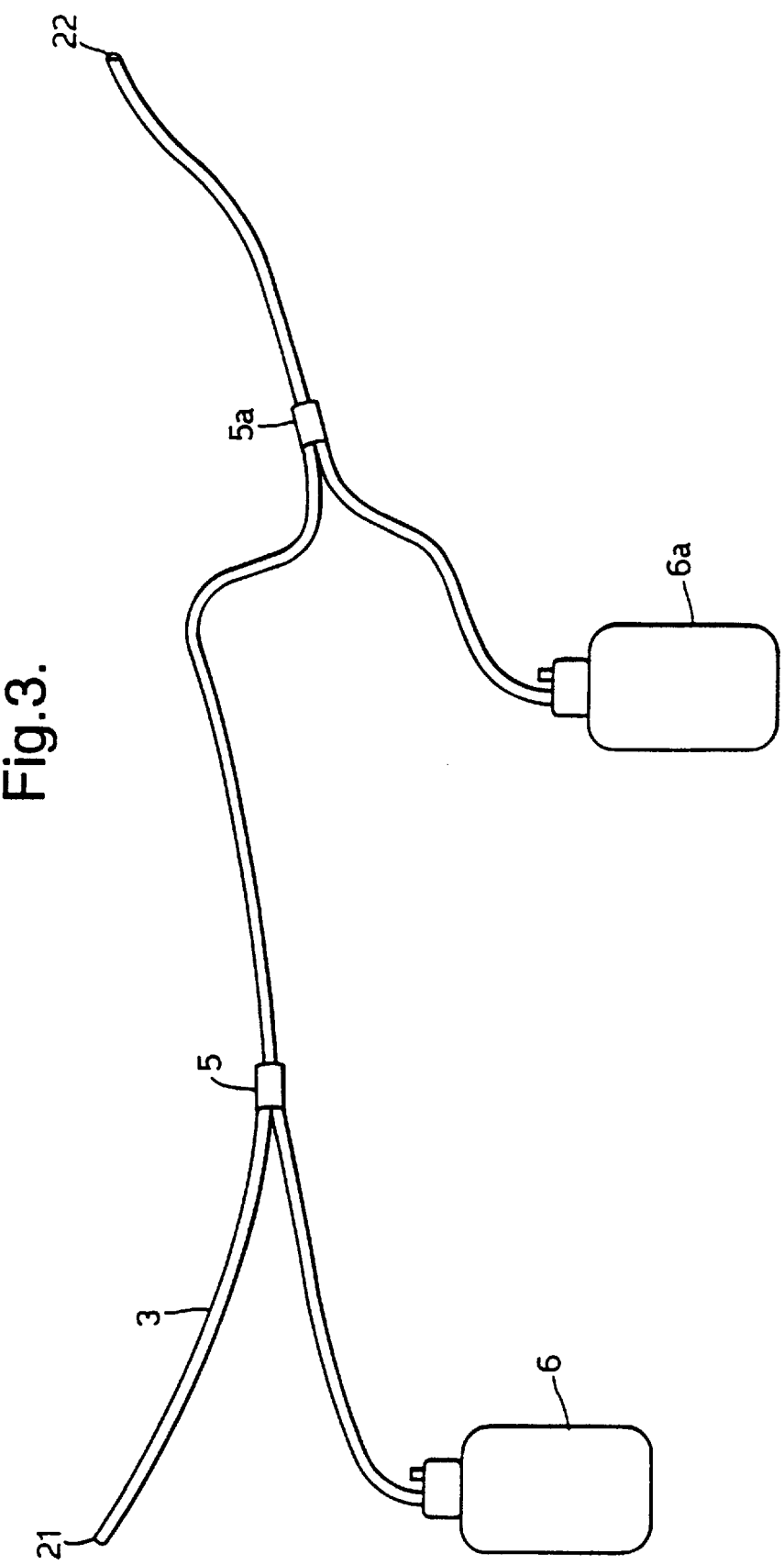
FIG. 3 shows a tubing element and reagent container network further described in Example 2.
Figure 4:
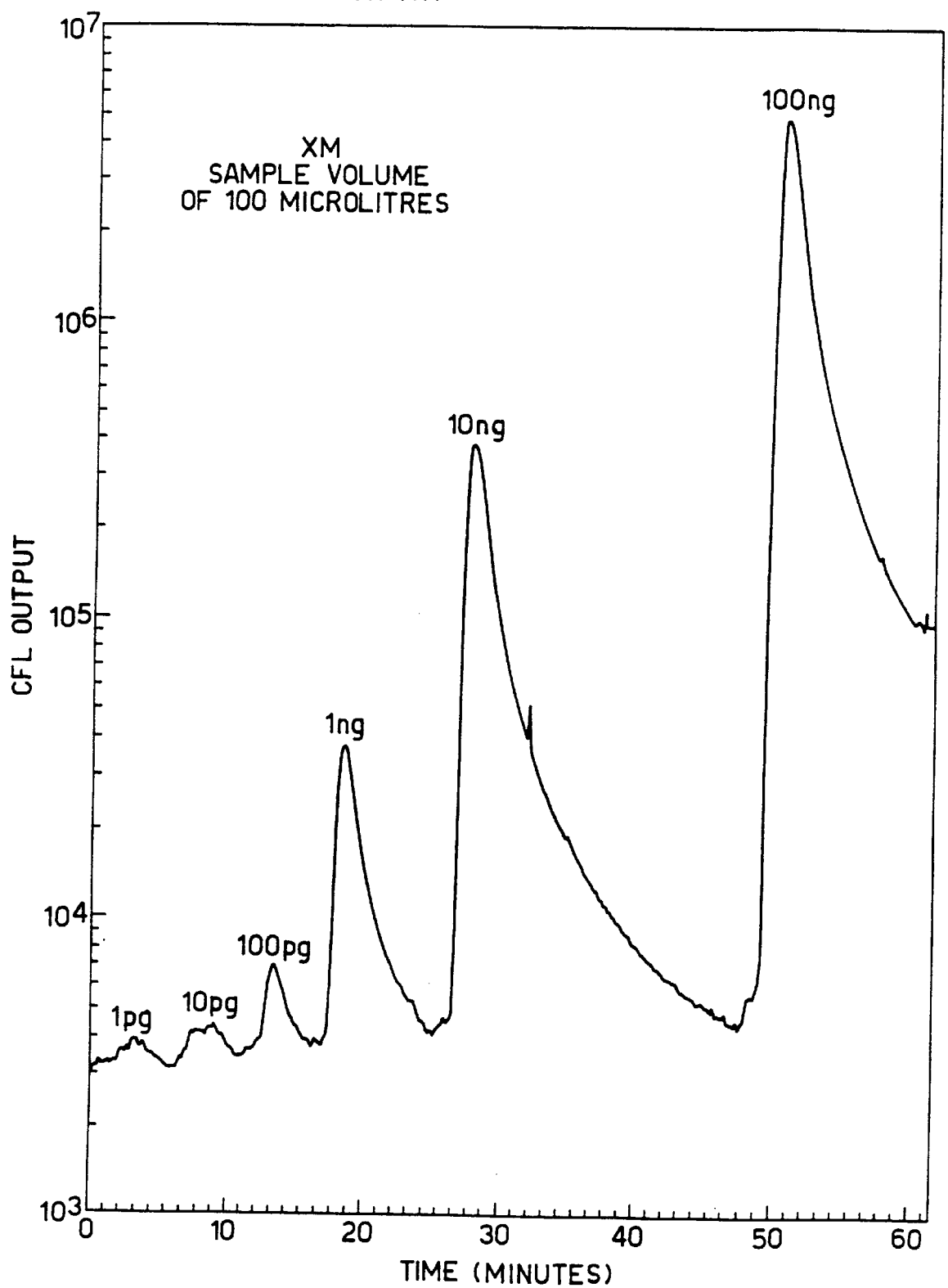
FIG. 4 is a graph in counts per minute output of the luminometer described in Example 1.

The preferred apparatus of the invention as shown in FIG. 2 uses feedback from the interface to control liquid addition to the cyclone.

I claim:

1. A method for determining the presence and/or amount of cellular material present in a gaseous environment comprising:
   (a) continuously collecting a particulate fraction from that environment over a period of time;
   (b) continuously transferring the particulate fraction to a processing fluid;
   (c) continuously releasing intracellular contents including ATP from microorganisms, cells or spores present in the processing fluid containing the particulate fraction using a lytic agent;
   (d) continuously adding luminescent reagents which cause the processing fluid to luminesce in the presence of ATP;
   (e) measuring light emitted form the processing fluid produced in (d) in a luminometer wherein a signal indicative of this light is produced by the luminometer and the presence and magnitude of the signal is equated to presence and/or amount of cellular material present in the gas.

2. A method as claimed in claim 1 wherein the material comprises bacterial cells or eucaryotic cells.

3. A method as claimed in claim 1 wherein the gas is atmospheric air.

4. A method as claimed in claim 1 wherein the lytic agent is a detergent or an enzyme.

5. A method as claimed claim 1 wherein step (b) is carried out using an energy source.

6. A method as claimed in claim 5 wherein the energy source is heat or sound source.

7. A method as claimed in claim 1 wherein the processing fluid is a liquid which is passed by peristaltic pumps from the collecting step to the other steps via one or more peristaltic tubing conduits.

8. A method as claimed in claim 1 wherein the step (b) produces processing fluid in two separate streams and the step (c) is carried out by use of different means in each flow; whereby in a first one of the flows all cellular material has its intracellular contents released and in a second one of the flows eucaryotic cells and fungal spores have their intracellular contents released; the signal generated from luminometer light detector in the second flow is subtracted from that of the first and related to a number of bacteria present in the gas taken into the collection step.

9. A method as claimed in claim 8 wherein the first one of the flows is treated with cationic detergent and the second one of the flows is treated with non-ionic detergent.

10. A method as claimed in claim 1 wherein adenosine diphosphate (ADP) is added to the processing fluid such as to be converted by any adenylate kinase present in the intracellular contents released in step (c) into adenosine triphosphate which in turn is detected in step (e).

11. An apparatus comprising
   (a) a cyclone or virtual impactor for continuously collecting a particulate fraction from a gaseous environment;
   (b) a means for continuously transferring the particulate fraction to a processing fluid;
   (c) a device for adding lytic agent for continuously releasing intracellular contents including ATP from cellular material present in the processing fluid;
   (d) a means for continuously adding luminescent reagents, dependent upon presence of ATP to effect luminescence, to the processing fluid;
   (e) a light detector means adapted to be with the processing fluid from step (d) and capable of emitting a signal indicative of the occurrence and amount of luminescence detected thereby; and
   (g) a signal transmitting means for feeding the signal from the luminometer to a processor and/or display means for indicating the presence and or amount of microorganism cells or spores.

12. An apparatus as claimed in claim 11 which comprises a cyclone capable of processing over 100 liters of air per minute for collecting a particulate fraction.

13. An apparatus as claimed in claim 12 wherein the cyclone is capable of processing between 500 and 2000 liters of air per minute.

14. An apparatus as claimed in claim 13 wherein the cyclone processes about 1000 liters of air per minute.

15. An apparatus as claimed in claim 11 wherein the cyclone is a wet walled hydrocyclone.

16. An apparatus as claimed in claim 11 wherein the collecting means is a high velocity virtual impactor capable of processing between 50 and 150 liters of air per minute.

17. An apparatus as claimed in claims 11 which further comprises fluid which is a liquid.

18. An apparatus as claimed in claim 17 wherein the liquid is water or a buffer.

19. An apparatus as claimed in claim 18 wherein the water or buffer contains ADP and/or reagent for releasing intracellular contents including ATP from cells.

20. An apparatus as claimed in claim 11 further comprising a gas liquid interface that is capable of maintaining the dilution of the particulate in the processing fluid at a substantially constant level and/or removing excess air as bubbles.

21. An apparatus as claimed in claim 11 wherein the means (c) for releasing intracellular content including ATP includes a heater, sonic device or device for adding a lytic agent.

22. An apparatus as claimed in claim 11 wherein the processing fluid is transferred between means in a conduit.

23. An apparatus as claimed in claim 22 wherein the fluid is a liquid, the conduit comprises peristaltic tubing and the apparatus includes peristaltic pumps for acting upon this to drive the processing liquid from means to means.

24. An apparatus as claimed in claim 23 wherein the means for releasing intracellular contents and/or supplying ADP comprises a supply of lytic agent and/or ADP reagent which is mixed with the processing liquid at a junction of the peristaltic tubing from the collecting means with tubing from the supply of lytic agent and/or ADP reagent.

25. An apparatus as claimed in claim 24 wherein the junction is at a manifold or at a junction between pieces of peristaltic tubing.

26. An apparatus as claimed in claim 11 wherein the luminescence reagents are mixed with the processing fluid in the luminometer light measuring device.

27. An apparatus as claimed in claim 11 wherein the processing fluid is provided as two flows, each flow passing through a respective intracellular contents releasing means capable of releasing ATP or adenylate kinase from either eucaryotic cells and fungal spores or all cellular material, and subsequently passing these flows into respective luminometer light measuring chambers where luminescence reagent adding means provide for emmision of light in the presence of ATP; the amount of light detected in the measuring chambers being detected by light detectors which emit electrical signals to a processing or display or print out means.

28. An apparatus as claimed in claim 27 wherein the signal from the eucaryotic cells and fungal spores line is subtracted from the all cellular material line and the value left indicated on a display means or print out means.

29. An apparatus as claimed in claim 11 wherein the luminescence reagents include luciferase and this is immobilised near the luminometer light detector within the light measuring chamber where the processing fluid and luminescence reagents are mixed.

30. A tubing element or network of such elements suitable for use in the apparatus of the invention comprising a peristaltic tubing element or network of such elements characterised in that the element or network has a first tubing length with a free end suitable for attachment to the fluid outlet of an apparatus for continuously collecting a particulate fraction from a gaseous environment , a junction between the other end of the first tubing length and a second tubing length, the second tubing length being suitable for connection to a source of reagent, and a further tubing length provided leading from the junction of the first and second lengths having a free end suitable for connection to an inlet means of a luminometer chamber; all the lengths being capable of peristaltic action under influence of a peristaltic pump.

31. A tubing element or network as claimed in claim 30 characterised in that the free ends of the tubing are covered to exclude entry of cellular materials by a puncturable or removable end cover.

32. An element or network as claimed in claim 30 wherein the free ends to the reagents are attached to reagent containers such that a sterile tubing network might be connected to an apparatus of claim 16 with the amounts and concentrations of the various reagents being matched to each other such that they last similar lengths of operation time when the apparatus is used for performing a method as claimed in claim 1.

* * * * *